US012653518B2

(12) United States Patent
     Malany

(10) Patent No.: US 12,653,518 B2
(45) Date of Patent: Jun. 16, 2026

(54) EXPERIMENTAL CHIP

(71) Applicant: Micro-gRx, Inc, Orlando, FL (US)

(72) Inventor: LeGrand K. Malany, Springfield, IL (US)

(73) Assignee: Micro-gRx, Inc., Orlando, FL (US)

( * ) Notice: Subject to any disclaimer, the term of this patent is extended or adjusted under 35 U.S.C. 154(b) by 701 days.

(21) Appl. No.: 18/151,916

(22) Filed: Jan. 9, 2023

(65) Prior Publication Data

US 2023/0225722 A1     Jul. 20, 2023

Related U.S. Application Data

(60) Provisional application No. 63/301,183, filed on Jan. 20, 2022.

(51) Int. Cl.
     *C12M 1/00*     (2006.01)
     *A61B 17/04*    (2006.01)
     *C12M 1/42*     (2006.01)
     *C12M 3/06*     (2006.01)

(52) U.S. Cl.
     CPC ......... *A61B 17/0401* (2013.01); *C12M 23/16* (2013.01); *C12M 23/34* (2013.01); *C12M 35/02* (2013.01); *A61B 2017/0412* (2013.01)

(58) Field of Classification Search
     None
     See application file for complete search history.

(56) References Cited

U.S. PATENT DOCUMENTS

2010/0112690 A1 *  5/2010  Eddington ............. C12M 23/12
                                                    435/297.5
2013/0203086 A1 *  8/2013  Achyuta ............ G01N 33/5058
                                                    435/7.1
2013/0295601 A1 * 11/2013  Park ...................... C12M 21/08
                                                    435/287.9
2014/0274739 A1 *  9/2014  Rinker ................ C12Q 1/6876
                                                    435/7.4
2016/0097027 A1 *  4/2016  Nikkhah ............... C12M 23/16
                                                    435/32
2019/0039069 A1 *  2/2019  Marshall .......... G01N 27/44791
2020/0378952 A1 * 12/2020  Prabhakarpandian ......................
                                                    G01N 33/50
2021/0054321 A1 *  2/2021  Nikkhah ............... C12M 21/08

* cited by examiner

*Primary Examiner* — Henry H Nguyen
(74) *Attorney, Agent, or Firm* — Parsons Behle & Latimer

(57)              ABSTRACT

An apparatus comprising a body having an inner cavity. First and second pluralities of anchor pins are positioned within in the inner cavity. The inner cavity includes a central cavity between the anchor pins. The inner cavity includes a media channel outside of the anchor pins. The media channel is in fluid communication with the central cavity through openings between the anchor pins. The anchor pins restrict complete fluid transfer while allowing molecular migration between the media channel and the central cavity. Posts are positioned in the central cavity and tissue may be connected between the posts. First and second ports are positioned in the central cavity and enable tissue to be positioned within the inner cavity. Third and fourth ports are located in the exterior of the body. The third and fourth ports are in fluid communication with the media channel.

19 Claims, 4 Drawing Sheets

EXPERIMENTAL CHIP

RELATED APPLICATION

This application claims the benefit of priority under 35 U.S.C. § 119 to U.S. Provisional Patent Application Ser. No. 63/301,183 entitled "EXPERIMENTAL CHIP" filed on Jan. 20, 2022, which is incorporated herein in its entirety.

FIELD OF THE DISCLOSURE

This disclosure is generally related to an experimental chip for biology research. The experimental chip is a microfluidic chip that allows electric stimulation of tissue positioned within the chip

BACKGROUND

It may be important to do research on tissue, which may be human muscle tissue. It is unknown how microgravity effects the tissue, such as the growth, regeneration, and stimulation of such tissue. While studying the microgravity of space on tissue there is not a well-known device that permits the study of tissue while also providing for the stimulation of such tissue as well as the capability of providing fluids to the tissue. Other disadvantages may exist.

SUMMARY

The disclosure is generally related to an experimental chip for biology research. The experimental chip is a microfluidic chip that allows electric stimulation of tissue positioned within the chip.

One example of the present disclosure is an apparatus comprising a body having an inner cavity. The apparatus includes a first plurality of anchor pins positioned within in the inner cavity and includes a second plurality of anchor pins within the inner cavity. The inner cavity of the apparatus has a central cavity between the first plurality of anchor pins and the second plurality of anchor pins. The inner cavity of the apparatus has a media channel outside of the first plurality of anchor pins and outside the second plurality of anchor pins. The media channel is in fluid communication with the central cavity through openings between the individual pins of the first plurality of anchor pins and through openings between the individual pins of the second plurality of anchor pins. The anchor pins restrict complete fluid transfer and allow molecular migration between the media channel and the central cavity. The apparatus includes a first post positioned in the central cavity and a second post positioned in the central cavity. The apparatus includes a first port positioned in the central cavity and a second port positioned in the central cavity. The first and second ports enable tissue to be positioned within the inner cavity. The apparatus includes a third port in the exterior of the body and a fourth port in the exterior of the body. The third port and the fourth port each being in fluid communication with the media channel. The third and fourth ports enable fluid to be injected into the media channel to enable molecular transfer between cavities for cellular health and maintenance within the central cavity. For example, fluid may be injected into the central cavity via the media channel to provide nutrients to tissue positioned within the central cavity.

Tissue may be connected between the first and second posts within the inner cavity. The apparatus may include a first electrode. The first end of the first electrode may extend from the body. A second end of the first electrode may be positioned adjacent to the inner cavity. The apparatus may include a second electrode. The first end of the second electrode may extend from the body. A second end of the second electrode may be positioned adjacent to the inner cavity. Tissue may be positioned within the central cavity via the first port and the second port. Tissue may be connected between the first and second posts. Fluid may be injected into the inner cavity via the third port or via the fourth port. Tissue connected between the first and second posts may be stimulated via the first electrode and via the second electrode.

One embodiment is an apparatus that includes a body having a first cavity, a first plurality of anchor pins positioned within in the first cavity, and a second plurality of anchor pins within the first cavity. The first cavity having a first central cavity between the first plurality of anchor pins and the second plurality of anchor pins. The first cavity also includes a first media channel positioned outside of the first plurality of anchor pins and positioned outside the second plurality of anchor pins with respect to the first central cavity. The first media channel is in fluid communication with the first central cavity through openings between the individual pins of the first plurality of anchor pins and through openings between the individual pins of the second plurality of anchor pins. The anchor pins restrict complete fluid transfer and allow molecular migration between the media channel and the central cavity. The apparatus includes a first post positioned in the first central cavity and a second post positioned in the first central cavity. The apparatus includes a first port in communication with the first media channel a second port in communication with the first media channel.

The apparatus may include a first electrode positioned adjacent to the first cavity. The apparatus may include a second electrode positioned adjacent to the first cavity. Tissue may be positioned within the first central cavity. The tissue may be connected between the first post and the second post. Fluid may be injected into the first media channel of the first cavity via the first and second ports allowing for molecular transfer between cavities through the openings between the individual pins of the first plurality of anchor pins and the opening between the individual pins of the second plurality of anchor pins. The tissue may be stimulated via the first electrode and via the second electrode.

The apparatus may include a second cavity in the body, a third plurality of anchor pins positioned within in the second cavity, and a fourth plurality of anchor pins within the second cavity. The second cavity may include a second central cavity between the third plurality of anchor pins and the fourth plurality of anchor pins. The second cavity may include a second media channel positioned outside of the third plurality of anchor pins and positioned outside the fourth plurality of anchor pins with respect to the second central cavity. The second media channel may be in fluid communication with the second central cavity through openings between the individual pins of the third plurality of anchor pins and through openings between the individual pins of the fourth plurality of anchor pins. The anchor pins restrict complete fluid transfer while allowing molecular migration between the media channel and the central cavity.

The apparatus may include a third post positioned in the second central cavity. The apparatus may include a fourth post positioned in the second central cavity. The apparatus may include a third port in communication with the second media channel. The apparatus may include a fourth port in communication with the second media channel. The apparatus may include a third electrode and a fourth electrode positioned adjacent to the second cavity. Tissue may be positioned within the second central cavity between the third and fourth posts. The tissue may be stimulated with the third and fourth electrodes. The third port may enable input into the second media channel and the fourth port may enable output from the second media channel for flow of fluid allowing molecular transfer between cavities for cellular health and maintenance within the central cavity.

The apparatus may include a third cavity in the body, a fifth plurality of anchor pins positioned within in the third cavity, and a sixth plurality of anchor pins within the third cavity. The third cavity may have a third central cavity between the fifth plurality of anchor pins and the sixth plurality of anchor pins. The third cavity may include a third media channel positioned outside of the fifth plurality of anchor pins and positioned outside the sixth plurality of anchor pins with respect to the third central cavity. The third media channel may be in fluid communication with the third central cavity through openings between the individual pins of the fifth plurality of anchor pins and through openings between the individual pins of the sixth plurality of anchor pins. The anchor pins restrict complete fluid transfer while allowing molecular migration between the media channel and the central cavity.

The apparatus may include a fifth post positioned in the third central cavity. The apparatus may include a sixth post positioned in the third central cavity. The apparatus may include a fifth port in communication with the third media channel. The apparatus may include a sixth port in communication with the third media channel. The apparatus may include a fifth electrode and a sixth electrode positioned adjacent to the third cavity. Tissue may be positioned within the third central cavity between the fifth and sixth posts. The tissue may be stimulated with the fifth and sixth electrodes. The fifth port may enable input into the third media channel and the sixth port may enable output from the third media channel for flow of fluid allowing molecular transfer between cavities for cellular health and maintenance within the central cavity.

The apparatus may include a fourth cavity in the body, a seventh plurality of anchor pins positioned within in the fourth cavity, and an eighth plurality of anchor pins within the fourth cavity. The fourth cavity may have a fourth central cavity between the seventh plurality of anchor pins and the eighth plurality of anchor pins. The fourth cavity may include a fourth media channel positioned outside of the seventh plurality of anchor pins and positioned outside the eighth plurality of anchor pins with respect to the fourth central cavity. The fourth media channel may be in fluid communication with the fourth central cavity through openings between the individual pins of the seventh plurality of anchor pins and through openings between the individual pins of the eighth plurality of anchor pins. The anchor pins restrict complete fluid transfer while allowing molecular migration between the media channel and the central cavity.

The apparatus may include a seventh post positioned in the fourth central cavity. The apparatus may include an eighth post positioned in the fourth central cavity. The apparatus may include a seventh port in communication with the fourth media channel. The apparatus may include an eighth port in communication with the fourth media channel. The apparatus may include a seventh electrode and an eighth electrode positioned adjacent to the fourth cavity. Tissue may be positioned within the fourth central cavity between the seventh and eighth posts. The tissue may be stimulated with the seventh and eighth electrodes. The seventh port may enable input into the fourth media channel and the eighth port may enable output from the fourth media channel for flow of fluid allowing molecular transfer between cavities for cellular health and maintenance within the central cavity. Other embodiments also exist.

Figure 1:
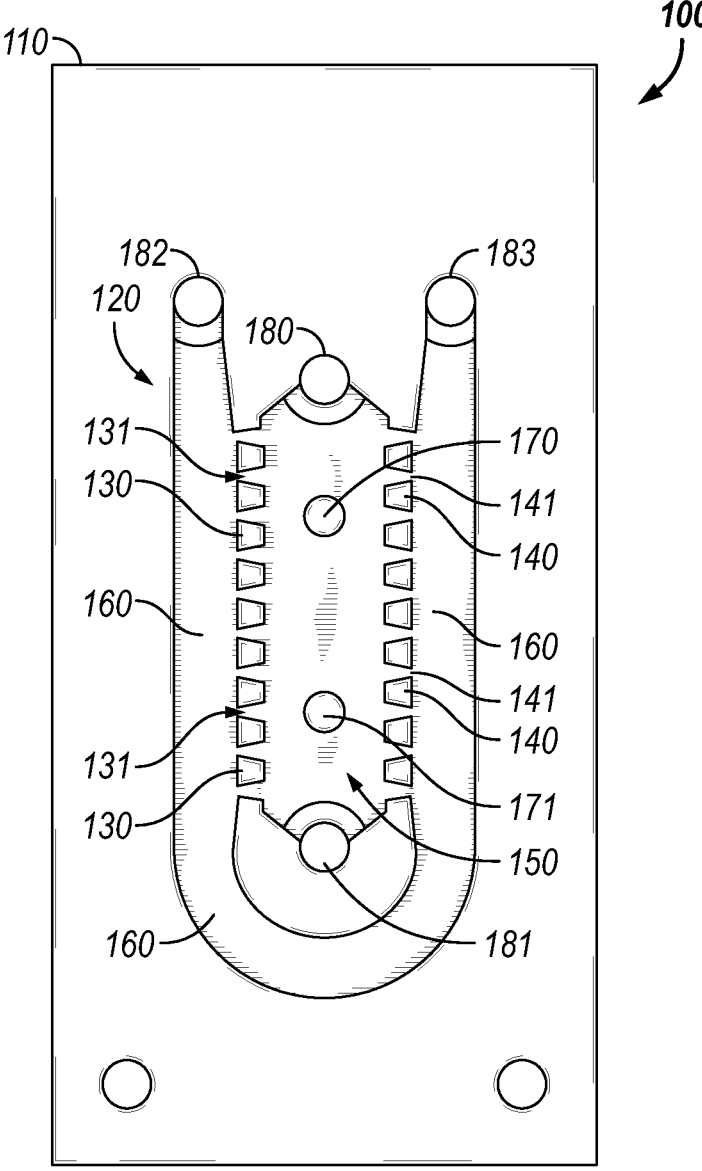
FIG. 1 shows an embodiment of an experimental chip.

While the disclosure is susceptible to various modifications and alternative forms, specific examples have been shown by way of example in the drawings and will be described in detail herein. However, it should be understood that the disclosure is not intended to be limited to the particular forms disclosed. Rather, the intention is to cover all modifications, equivalents and alternatives falling within the scope of the disclosure.

DETAILED DESCRIPTION

Figure 2:
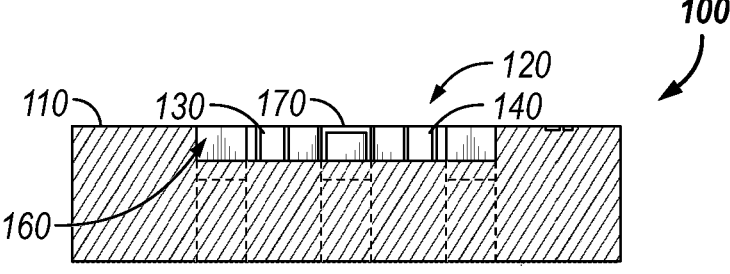
FIG. 2 is an end cross-sectional view of the experimental chip of FIG. 1.

FIG. 1 shows an experimental chip, or apparatus, 100. FIG. 2 shows an end cross-section view of the experimental chip 100. The experimental chip 100, includes a body 110 having an inner cavity 120. The body 110 may be transparent and may be comprised of glass, plastic, elastomer, acrylic, or the like. The experimental chip 100 may include a lid 111 to cover the inner cavity 120 as shown in FIG. 2. The lid 111 is not shown in FIG. 1 for clarity purposes. The lid 111 is transparent and may be comprised of various materials such as plastic, glass, elastomer, acrylic, or the like. The experimental chip 100 includes a first plurality of anchor pins 130 positioned within in the inner cavity 120. The experimental chip 100 includes a second plurality of anchor pins 140 positioned within the inner cavity 120. The inner cavity 120 includes a central cavity 150 between the first plurality of anchor pins 130 and the second plurality of anchor pins 140. The inner cavity 120 of the experimental chip 100 includes a media channel 160. The media channel 160 is positioned outside of the first plurality of anchor pins 130 and outside the second plurality of anchor pins 140. The media channel 160 may be used to provide flow of compounds to feed tissue cells and/or to introduce drugs to preserve tissue cells located within the central cavity 150. The media channel 160 is in fluid communication with the central cavity 150 through openings 131 between the individual pins of the first plurality of anchor pins 130 and through openings 141 between the individual pins of the second plurality of anchor pins 140. The first plurality of anchor pins 130 and the second plurality of anchor pins 140 restrict complete fluid transfer while allowing molecular migration between the media channel 160 and the central cavity 150. The experimental chip 100 includes a first post 170 positioned in the central cavity 150 and a second post 171 positioned in the central cavity 150.

The experimental chip 100 includes a first port 180 positioned in the central cavity 150 and a second port 181 positioned in the central cavity 150. The first and second ports 180, 181 enable tissue 200 (shown in FIG. 5) to be positioned within the inner cavity 150. For example, tissue cells seeded within a gel, such as a hydrogel, may be injected into the central cavity 150 via the first port 180 and/or the second port 181. The anchor pins 130, 140 restrict the migration of tissue cells from the central cavity 150 to the media channel 160.

The experimental chip 100 includes a third port 182 in the exterior of the body 110 and a fourth port 183 also in the exterior of the body 110. The third port 182 and the fourth port 183 are each in fluid communication with the media channel 160. The third and fourth ports 182, 183 enable fluid to be injected into the media channel 160. For example, fluid may be injected into the central cavity 150 via the media channel 160 to provide nutrients to tissue 200 positioned within the central cavity 150. The anchor pins 130, 140 prevent complete fluid transfer while permitting molecular migration between the media channel 160 and the central cavity 150. Tissue 200 may be connected between the first and second posts 170, 171 within the central cavity 150.

Figures 3, 4:
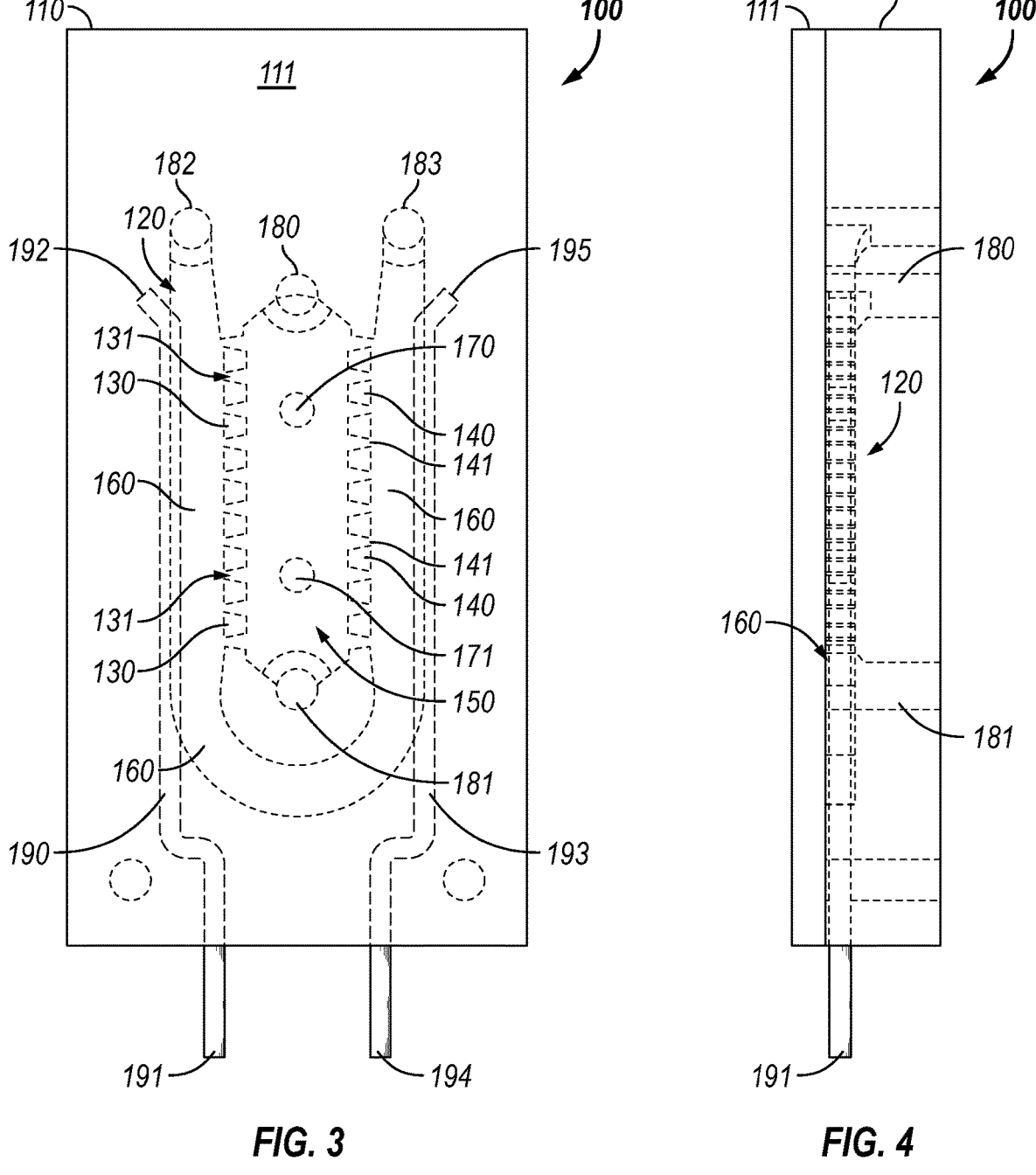
FIG. 3 shows an embodiment of an experimental chip.
FIG. 4 is a side cross-sectional view of the experimental chip of FIG. 3.

FIG. 3 shows an experimental chip 100. FIG. 4 shows a side cross-section view of the experimental chip 100 of FIG. 3. The experimental chip 100, includes a body 110 having an inner cavity 120. The experimental chip 100 includes a first plurality of anchor pins 130 positioned within in the inner cavity 120. The experimental chip 100 includes a second plurality of anchor pins 140 positioned within the inner cavity 120. The inner cavity 120 includes a central cavity 150 between the first plurality of anchor pins 130 and the second plurality of anchor pins 140. The inner cavity 120 of the experimental chip 100 includes a media channel 160. The media channel 160 is positioned outside of the first plurality of anchor pins 130 and outside the second plurality of anchor pins 140. The media channel 160 is in fluid communication with the central cavity 150 through openings 131 between the individual pins of the first plurality of anchor pins 130 and through openings 141 between individual pins of the second plurality of anchor pins 140. The anchor pins 130, 140 restrict complete fluid transfer while permitting molecular migration between the media channel 160 and the central cavity 150. The experimental chip 100 includes a first post 170 positioned in the central cavity 150 and a second post 171 positioned in the central cavity 150.

The experimental chip 100 includes a first port 180 positioned in the central cavity 150 and a second port 181 positioned in the central cavity 150. The first and second ports 180, 181 enable tissue 200 to be positioned within the inner cavity 150.

The experimental chip 100 includes a third port 182 in the exterior of the body 110 and a fourth port 183 in the exterior of the body 110. The third port 182 and the fourth port 183 are each in fluid communication with the media channel 160. The third and fourth ports 182, 183 enable fluid to be injected into the media channel 160. For example, fluid may be injected into the media channel 160 to provide nutrients to tissue 200 positioned within the central cavity 150. The anchor pins 130, 140 prevent complete fluid transfer while allowing molecular migration between the media channel 160 and the central cavity 150.

The experimental chip 100 includes a first electrode 190. A first end 191 of the first electrode 190 extends from the body 110. The first end 191 of the first electrode 190 is connected to a power source as would be appreciated by one of ordinary skill in the art having the benefit of this disclosure. A second end 192 of the first electrode 190 is positioned within the body 110 of the experimental chip 100. The second end 192 of the first electrode 190 is positioned adjacent to the inner cavity 120 of the experimental chip 100. The experimental chip 100 includes a second electrode

193. A first end 194 of the second electrode 193 extends from the body 110. The first end 194 of the second electrode 193 is connected to a power source as would be appreciated by one of ordinary skill in the art having the benefit of this disclosure. A second end 195 of the second electrode 193 is positioned within the body 110 of the experimental chip 100. The second end 195 of the second electrode 193 is positioned adjacent to the inner cavity 120 of the experimental chip 100. Tissue 200 positioned within the central cavity 150 of the experimental chip 100 may be stimulated by the first and second electrodes 190, 193 as would be appreciated by one of ordinary skill in the art having the benefit of this disclosure.

Figure 5:
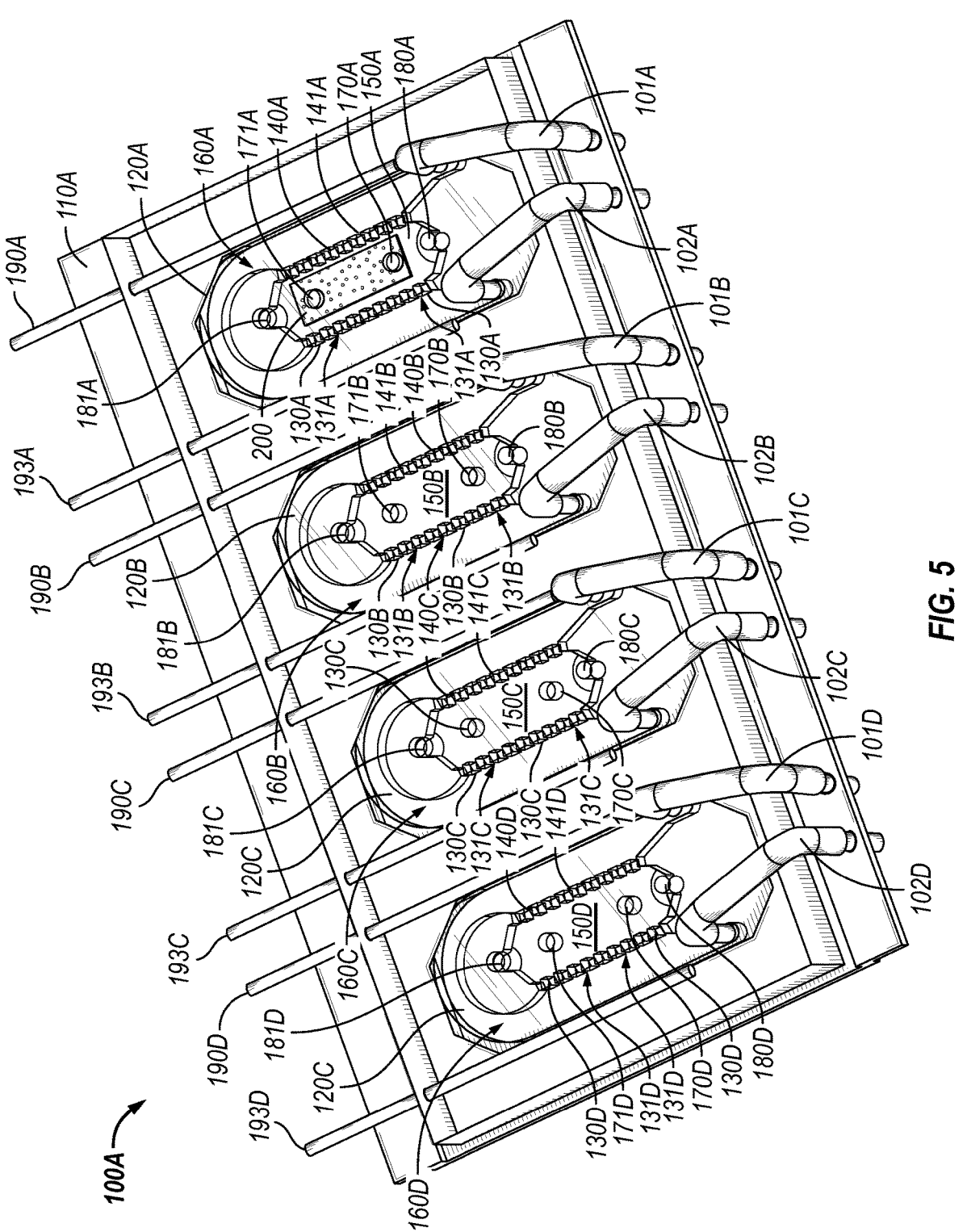
FIG. 5 shows an embodiment of an experimental chip.

FIG. 5 shows an embodiment of an apparatus, or experimental chip, 100A. The experimental chip 100A includes a body 110A having a first cavity 120A. The experimental chip 100A includes a first plurality of anchor pins 130A positioned within in the first cavity 120A. The experimental chip 100A includes a second plurality of anchor pins 140A within the first cavity 120A. The first cavity 120A includes a first central cavity 150A between the first plurality of anchor pins 130A and the second plurality of anchor pins 140A. The first cavity 120A also includes a first media channel 160A positioned outside of the first plurality of anchor pins 130A and positioned outside the second plurality of anchor pins 140A with respect to the first central cavity 150A. The first media channel 160A is in fluid communication with the first central cavity 150A through openings 131A between the individual pins of the first plurality of anchor pins 130A and through openings 141A between the individual pins of the second plurality of anchor pins 140A. The anchor pins 130A, 140A restrict complete fluid transfer while allowing molecular migration between the first media channel 160A and the first central cavity 150A. The experimental chip 100A includes a first post 170A positioned in the first central cavity 150A and a second post 171A positioned in the first central cavity 150A. The experimental chip 100A includes a first port 182A in communication with the first media channel 160A a second port 183A in communication with the first media channel 160A. The experimental chip 100A includes a first conduit 101A in communication with the first port 182A and a second conduit 102A in communication with the second port 183A. Fluid may be injected into and out of the first media channel 160A via the first port 182A, the first conduit 101A, the second port 183A, and the second conduit 102A.

The experimental chip 100A includes a first electrode 190A positioned adjacent to the first cavity 120A. The experimental chip 100A includes a second electrode 193A also positioned adjacent to the first cavity 120A. Tissue 200 may be positioned within the first central cavity 150A as would be appreciated by one of ordinary skill in the art having the benefit of this disclosure. FIG. 5 shows schematically tissue 200 connected between the first post 170A and the second post 171A. Fluid may be injected into the first port 182A allowing for molecular transfer between cavities through the openings 131A between the individual pins of the first plurality of anchor pins 130A and the openings 141A between the individual pins of the second plurality of anchor pins 140A. The tissue 200 may be stimulated via the first electrode 190A and via the second electrode 193A.

The experimental chip 100A includes a second cavity 120B in the body 110A. The experimental chip 100A includes a third plurality of anchor pins 130B positioned within in the second cavity 120B and a fourth plurality of anchor pins 140B within the second cavity 120B. The second cavity 120B includes a second central cavity 150B between the third plurality of anchor pins 130B and the fourth plurality of anchor pins 140B. The second cavity 120B includes a second media channel 160B positioned outside of the third plurality of anchor pins 130B and positioned outside the fourth plurality of anchor pins 140B with respect to the second central cavity 150B. The second media channel 160B is in fluid communication with the second central cavity 150B through openings 131B between the individual pins of the third plurality of anchor pins 130B and through openings 141B between the individual pins of the fourth plurality of anchor pins 140B. The anchor pins 130B, 140B restrict complete fluid transfer while permitting molecular migration between the second media channel 160B and the second central cavity 150B.

The experimental chip 100A includes a third post 170B positioned in the second central cavity 150B. The experimental chip 100A includes a fourth post 171B positioned in the second central cavity 150B. The experimental chip 100A includes a third port 182B in communication with the second media channel 160B. The experimental chip 100A includes a fourth port 183B in communication with the second media channel 160B. The experimental chip 100A includes a third electrode 180B and a fourth electrode 183B positioned adjacent to the second cavity 120B. Tissue may be positioned within the second central cavity 150B between the third and fourth posts 170B, 171B. The tissue may be stimulated with the third and fourth electrodes 180B, 183B. The third port 182B enables input into the second media channel 160B and the fourth port 183B enables output from the second media channel 160B. The experimental chip 100A includes a third conduit 101B in communication with the third port 182B and a fourth conduit 102B in communication with the fourth port 183B. Fluid may be injected into and out of the second media channel 160B via the third port 182B, the third conduit 101B, the fourth port 183B, and the fourth conduit 102B for flow of fluid allowing molecular transfer between cavities for cellular health and maintenance within the central cavity.

The experimental chip 100A includes a third cavity 120C in the body 110A. The experimental chip 100A includes a fifth plurality of anchor pins 130C positioned within in the third cavity 120C and a sixth plurality of anchor pins 140C within the third cavity 120C. The third cavity 120C includes a third central cavity 150C between the fifth plurality of anchor pins 130C and the sixth plurality of anchor pins 140C. The third cavity 120C includes a third media channel 150C positioned outside of the fifth plurality of anchor pins 130C and positioned outside the sixth plurality of anchor pins 140C with respect to the third central cavity 150C. The third media channel 160C is in fluid communication with the third central cavity 150C through openings 131C between the individual pins of the fifth plurality of anchor pins 130C and through openings 141C between the individual pins of the sixth plurality of anchor pins 140C. The anchor pins 130C, 140C restrict complete fluid transfer while permitting molecular migration between the third media channel 160C and the third central cavity 150C.

The experimental chip 100A includes a fifth post 170C positioned in the third central cavity 150C. The experimental chip 100A includes a sixth post 171C positioned in the third central cavity 150C. The experimental chip 100A includes a fifth port 182C in communication with the third media channel 160C. The experimental chip 100A includes a sixth port 183C in communication with the third media channel 160C. The experimental chip 100A includes a fifth electrode 190C and a sixth electrode 193C positioned adjacent to the third cavity 120C. Tissue may be positioned within the third central cavity 150C between the fifth and sixth posts 170C, 171C. The tissue may be stimulated with the fifth and sixth electrodes 190C, 193C. The fifth port may enable input into the third media channel and the sixth port may enable output from the third media channel. The experimental chip 100A includes a fifth conduit 101C in communication with the fifth port 182C and a sixth conduit 102C in communication with the sixth port 183C. Fluid may be injected into and out of the media channel 160C via the fifth port 182C, the fifth conduit 101C, the sixth port 183C, and the sixth conduit 102C for flow of fluid allowing molecular transfer between cavities for cellular health and maintenance within the central cavity.

The experimental chip 100A includes a fourth cavity 120D in the body 110A. The experimental chip 100A includes a seventh plurality of anchor pins 130D positioned within in the fourth cavity 120D and an eighth plurality of anchor pins 140D within the fourth cavity 120D. The fourth cavity 120D includes a fourth central cavity 150D between the seventh plurality of anchor pins 130D and the eighth plurality of anchor pins 140D. The fourth cavity 120D includes a fourth media channel 160D positioned outside of the seventh plurality of anchor pins 130D and positioned outside the eighth plurality of anchor pins 140D with respect to the fourth central cavity 150D. The fourth media channel 160D is in fluid communication with the fourth central cavity 150D through openings 131D between the individual pins of the seventh plurality of anchor pins 130D and through openings 141D between the individual pins of the eighth plurality of anchor pins 140D. The anchor pins 130D, 140D restrict complete fluid transfer while permitting molecular migration between the fourth media channel 160D and the fourth central cavity 150D.

The experimental chip 100A includes a seventh post 170D positioned in the fourth central cavity 150D. The experimental chip 100A includes an eighth post 171D positioned in the fourth central cavity 150D. The experimental chip 100A include a seventh port 182D in communication with the fourth media channel 160D. The experimental chip 100A includes an eighth port 183D in communication with the fourth media channel 160D. The experimental chip 100A includes a seventh electrode 190D and an eighth electrode 193D positioned adjacent to the fourth cavity 120D. Tissue may be positioned within the fourth central cavity 150D between the seventh and eighth posts 170D, 171D. The tissue may be stimulated with the seventh and eighth electrodes 190D, 193D. The seventh port 182D may enable input into the fourth media channel 160D and the eighth port 183D may enable output from the fourth media channel 160D. The experimental chip 100A includes a seventh conduit 101D in communication with the seventh port 182D and an eighth conduit 102D in communication with the eighth port 183D. Fluid may be injected into and out of the fourth media channel 160D via the seventh port 182D, the seventh conduit 101D, the eighth port 183D, and the eighth conduit 102D for flow of fluid allowing molecular transfer between cavities for cellular health and maintenance within the central cavity. The multiple central cavities 150A-150D enable the comparison of different tissues. For example, different muscle tissues may be stimulated by the electrodes 180A-180D, 183A-183D for comparison.

Figure 6:
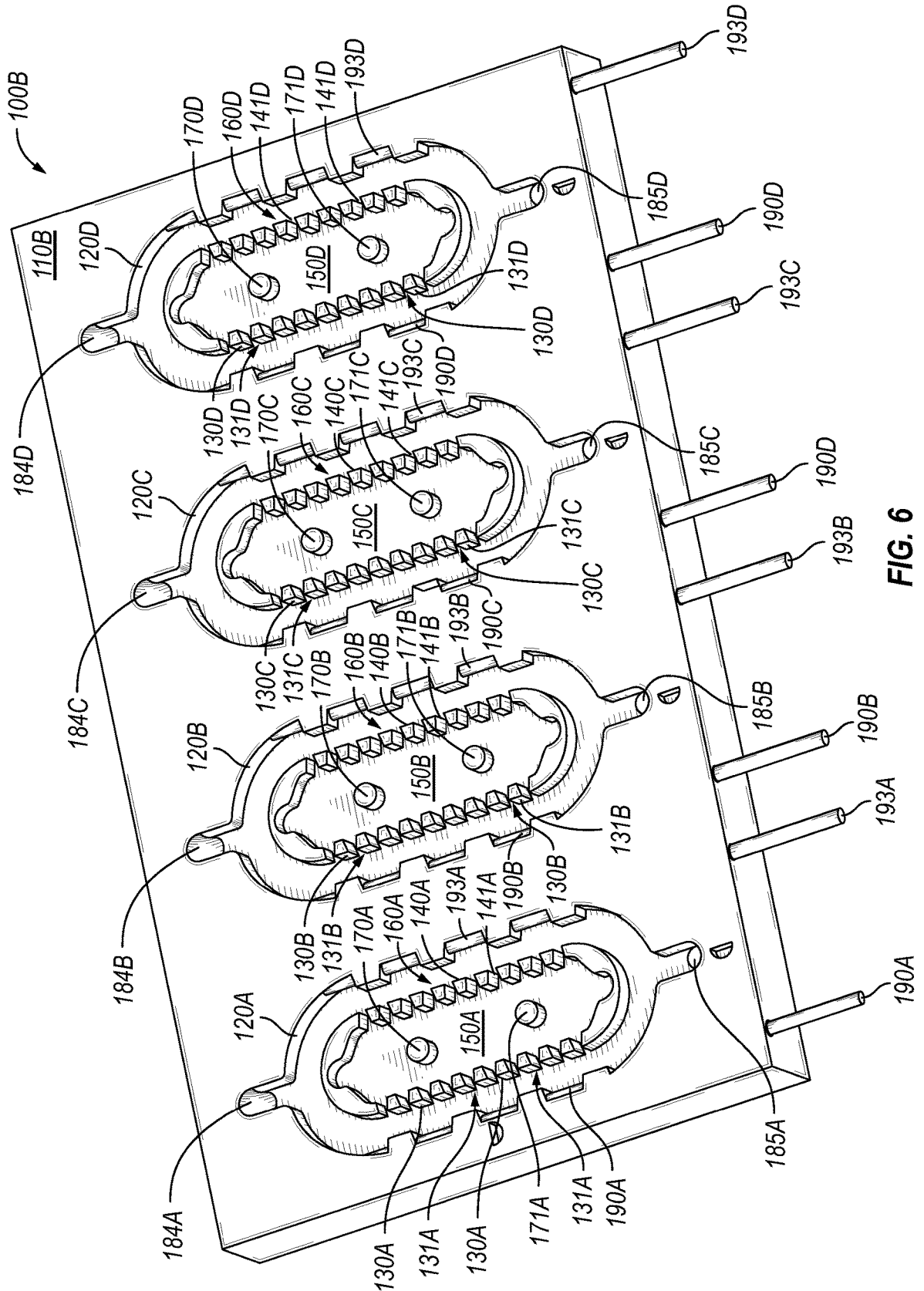
FIG. 6 shows an embodiment of an experimental chip.

FIG. 6 shows an embodiment of an apparatus, or experimental chip, 100B. The experimental chip 100B includes a body 110B having a first cavity 120A. The experimental chip 100B includes a first plurality of anchor pins 130A positioned within in the first cavity 120A. The experimental chip 100B includes a second plurality of anchor pins 140A within the first cavity 120A. The first cavity 120A includes a first central cavity 150A between the first plurality of anchor pins 130A and the second plurality of anchor pins 140A. The first cavity 120A also includes a first media channel 160A positioned outside of the first plurality of anchor pins 130A and positioned outside the second plurality of anchor pins 140A with respect to the first central cavity 150A. The first media channel 160A is in fluid communication with the first central cavity 150A through openings 131A between the individual pins of the first plurality of anchor pins 130A and through openings 141A between the individual pins of the second plurality of anchor pins 140A. The anchor pins 130A, 140A restrict complete fluid transfer while permitting molecular migration between the media channel 160A and the central cavity 150A. The experimental chip 100B includes a first post 170A positioned in the first central cavity 150A and a second post 171A positioned in the first central cavity 150A. The experimental chip 100B includes a first port 184A in communication with the first media channel 160A a second port 185A in communication with the first media channel 160A. The first port 184A may be an input port located at one end of the first cavity 120A and the second port 185A may be an output port located at the other end of the first cavity 120A. Fluid may be injected into the first media channel 160A via the first port 184A and fluid may be removed from the first media channel 160A via the second port 185A.

The experimental chip 100B includes a first electrode 190A positioned adjacent to the first cavity 120A. Portions of the first electrode 190A may be exposed to the first cavity 120A as shown in FIG. 6. The experimental chip 100B includes a second electrode 193A also positioned adjacent to the first cavity 120A. Portions of the second electrode 190A may be exposed to the first cavity 120A as shown in FIG. 6. Tissue may be positioned within the first central cavity 150A as would be appreciated by one of ordinary skill in the art having the benefit of this disclosure. The tissue may be connected between the first post 170A and the second post 171A. Fluid may be injected into the first port 184A allowing for molecular transfer between cavities through the openings 131A between the individual pins of the first plurality of anchor pins 130A and the openings 141A between the individual pins of the second plurality of anchor pins 140A. The tissue may be stimulated via the first electrode 190A and via the second electrode 193A.

The experimental chip 100B includes a second cavity 120B in the body 110B. The experimental chip 100B includes a third plurality of anchor pins 130B positioned within in the second cavity 120B and a fourth plurality of anchor pins 140B within the second cavity 120B. The second cavity 120B includes a second central cavity 150B between the third plurality of anchor pins 130B and the fourth plurality of anchor pins 140B. The second cavity 120B includes a second media channel 160B positioned outside of the third plurality of anchor pins 130B and positioned outside the fourth plurality of anchor pins 140B with respect to the second central cavity 150B. The second media channel 160B is in fluid communication with the second central cavity 150B through openings 131B between the individual pins of the third plurality of anchor pins 130B and through openings 141B between the individual pins of the fourth plurality of anchor pins 140B. The anchor pins 130B, 140B restrict complete fluid transfer while allowing molecular migration between the second media channel 160B and the second central cavity 150B.

The experimental chip 100B includes a third post 170B positioned in the second central cavity 150B. The experimental chip 100B includes a fourth post 171B positioned in the second central cavity 150B. The experimental chip 100B includes a third port 184B in communication with the second media channel 160B a fourth port 185B in communication with the second media channel 160B. The third port 184B may be an input port located at one end of the second cavity 120B and the fourth port 185B may be an output port located at the other end of the second cavity 120B. Fluid may be injected into the second media channel 160B via the third port 184B and fluid may be removed from the second media channel 160B via the fourth port 185B for flow of fluid allowing molecular transfer between cavities for cellular health and maintenance within the central cavity.

The experimental chip 100B includes a third electrode 190B positioned adjacent to the second cavity 120B. Portions of the third electrode 190B may be exposed to the second cavity 120B as shown in FIG. 6. The experimental chip 100B includes a fourth electrode 193B also positioned adjacent to the second cavity 120B. Portions of the fourth electrode 193B may be exposed to the second cavity 120B as shown in FIG. 6. Tissue may be positioned within the second central cavity 150B between the third and fourth posts 170B, 171B. The tissue may be stimulated with the third and fourth electrodes 190B, 193B. The third port 184B enables input into the second media channel 160B and the fourth port 185B enables output from the second media channel 160B for flow of fluid allowing molecular transfer between cavities for cellular health and maintenance within the central cavity.

The experimental chip 100B includes a third cavity 120C in the body 110B. The experimental chip 100B includes a fifth plurality of anchor pins 130C positioned within in the third cavity 120C and a sixth plurality of anchor pins 140C within the third cavity 120C. The third cavity 120C includes a third central cavity 150C between the fifth plurality of anchor pins 130C and the sixth plurality of anchor pins 140C. The third cavity 120C includes a third media channel 160C positioned outside of the fifth plurality of anchor pins 130C and positioned outside the sixth plurality of anchor pins 140C with respect to the third central cavity 150C. The third media channel 160C is in fluid communication with the third central cavity 150C through openings 131C between the individual pins of the fifth plurality of anchor pins 130C and through openings 141C between the individual pins of the sixth plurality of anchor pins 140C. The anchor pins 130C, 140C restrict complete fluid transfer while allowing molecular migration between the third media channel 160C and the third central cavity 150C.

The experimental chip 100B includes a fifth post 170C positioned in the third central cavity 150C. The experimental chip 100B includes a sixth post 171C positioned in the third central cavity 150C. The experimental chip 100B includes a fifth port 184C in communication with the third media channel 160C a sixth port 185C in communication with the third media channel 160C. The fifth port 184C may be an input port located at one end of the third cavity 120C and the sixth port 185C may be an output port located at the other end of the third cavity 120C. Fluid may be injected into the third media channel 160C via the fifth port 184C and fluid may be removed from the third media channel 160C via the sixth port 185C for flow of fluid allowing molecular transfer between cavities for cellular health and maintenance within the central cavity.

The experimental chip 100B includes a fifth electrode 190C positioned adjacent to the third cavity 120C. Portions of the fifth electrode 190C may be exposed to the third cavity 120C as shown in FIG. 6. The experimental chip 100B includes a sixth electrode 193C also positioned adjacent to the third cavity 120C. Portions of the sixth electrode 193C may be exposed to the third cavity 120C as shown in FIG. 6. Tissue may be positioned within the third central cavity 150C between the fifth and sixth posts 170C, 171C. The tissue may be stimulated with the fifth and sixth electrodes 190C, 193C. The fifth port 184C may enable input into the third media channel 160C and the sixth port 185C may enable output from the third media channel 160C for flow of fluid allowing molecular transfer between cavities for cellular health and maintenance within the central cavity.

The experimental chip 100B includes a fourth cavity 120D in the body 110B. The experimental chip 100B includes a seventh plurality of anchor pins 130D positioned within in the fourth cavity 120D and an eighth plurality of anchor pins 140D within the fourth cavity 120D. The fourth cavity 120D includes a fourth central cavity 150D between the seventh plurality of anchor pins 130D and the eighth plurality of anchor pins 140D. The fourth cavity 120D includes a fourth media channel 160D positioned outside of the seventh plurality of anchor pins 130D and positioned outside the eighth plurality of anchor pins 140D with respect to the fourth central cavity 150D. The fourth media channel 160D is in fluid communication with the fourth central cavity 150D through openings 131D between the individual pins of the seventh plurality of anchor pins 130D and through openings 141D between the individual pins of the eighth plurality of anchor pins 140D. The anchor pins 130D, 140D restrict complete fluid transfer while permitting molecular migration between the fourth media channel 160D and the fourth central cavity 150D.

The experimental chip 100B includes a seventh post 170D positioned in the fourth central cavity 150D. The experimental chip 100B includes an eighth post 171D positioned in the fourth central cavity 150D. The experimental chip 100B includes a seventh port 184D in communication with the fourth media channel 160D an eighth port 185D in communication with the fourth media channel 160D. The seventh port 184D may be an input port located at one end of the fourth cavity 120D and the eighth port 185D may be an output port located at the other end of the fourth cavity 120D. Fluid may be injected into the fourth media channel 160D via the seventh port 184D and fluid may be removed from the fourth media channel 160D via the eighth port 185D for flow of fluid allowing molecular transfer between cavities for cellular health and maintenance within the central cavity.

The experimental chip 100B includes a seventh electrode 190D positioned adjacent to the fourth cavity 120D. Portions of the seventh electrode 190D may be exposed to the fourth cavity 120D as shown in FIG. 6. The experimental chip 100B includes an eighth electrode 193D also positioned adjacent to the fourth cavity 120D. Portions of the eighth electrode 193D may be exposed to the fourth cavity 120D as shown in FIG. 6. Tissue may be positioned within the fourth central cavity 150D between the seventh and eighth posts 170D, 171D. The tissue may be stimulated with the seventh and eighth electrodes 190D, 193D. The seventh port 184D may enable input into the fourth media channel 160D and the eighth port 185D may enable output from the fourth media channel 160D for flow of fluid allowing molecular transfer between cavities for cellular health and maintenance within the central cavity.

Although various examples have been shown and described, the present disclosure is not so limited and will be understood to include all such modifications and variations as would be apparent to one skilled in the art.

What is claimed is:

1. An apparatus comprising:
a body having a first end, a second end, and an inner cavity;
a first plurality of anchor pins positioned within the inner cavity;
a second plurality of anchor pins within the inner cavity;
the inner cavity having a central cavity between the first plurality of anchor pins and the second plurality of anchor pins;
the inner cavity having a single media channel positioned outside of the first plurality of anchor pins and extending substantially continuously to a position outside the second plurality of anchor pins, the media channel in fluid communication with the central cavity through openings between individual pins of the first plurality of anchor pins and through openings between individual pins of the second plurality of anchor pins, wherein the openings between individual pins of the first plurality of anchor pins and the openings between individual pins of the second plurality of anchor pins restrict complete fluid transfer between the media channel and the central cavity and allow molecular migration between the media channel and the central cavity;
a first post positioned in the central cavity;
a second post positioned in the central cavity;
a first port positioned in the central cavity;
a second port positioned in the central cavity;
a third port in an exterior of the body located at the first end, the third port in fluid communication with the media channel; and
a fourth port in the exterior of the body located at the first end, the fourth port in fluid communication with the media channel; and
wherein the third port and the fourth port enable fluid to be injected into the media channel.

2. The apparatus of claim 1, further comprising a first electrode, a first end of the first electrode extends from the body and a second end of the first electrode is positioned adjacent to the inner cavity.

3. The apparatus of claim 2, further comprising a second electrode, a first end of the second electrode extends from the body and a second end of the second electrode is positioned adjacent to the inner cavity.

4. The apparatus of claim 3, wherein tissue is positionable within the central cavity via the first port and the second port.

5. The apparatus of claim 4, wherein tissue is connectable between the first and second posts.

6. The apparatus of claim 5, wherein fluid is injectable into media channel via the third port or via the fourth port for molecular transfer between the media channel and the central cavity.

7. The apparatus of claim 6, wherein the tissue is stimulatable via the first electrode and the second electrode.

8. An apparatus comprising:
a body having a first end, a second end, and a first cavity;
a first plurality of anchor pins positioned within the first cavity;
a second plurality of anchor pins within the first cavity;
the first cavity having a first central cavity between the first plurality of anchor pins and the second plurality of anchor pins;

the first cavity including a first media channel having a first leg positioned outside of the first plurality of anchor pins and extending substantially continuously to a second leg positioned outside the second plurality of anchor pins with respect to the first central cavity, the first media channel is in fluid communication with the first central cavity through openings between individual pins of the first plurality of anchor pins and through openings between individual pins of the second plurality of anchor pins, wherein the openings between individual pins of the first plurality of anchor pins and the openings between individual pins of the second plurality of anchor pins restrict complete fluid transfer between the first media channel and the first central cavity and allow molecular migration between the first media channel and the first central cavity;

a first post positioned in the first central cavity;

a second post positioned in the first central cavity;

a first port located in the first end of the body and in communication with the first media channel; and a second port located in the first end of the body and in communication with the first media channel.

9. The apparatus of claim 8, further comprising a first electrode and a second electrode positioned adjacent to the first cavity.

10. The apparatus of claim 9, wherein tissue is positionable within the first central cavity.

11. The apparatus of claim 10, wherein tissue is connectable between the first and second posts.

12. The apparatus of claim 11, wherein fluid is injectable into first media channel via the first port for molecular transfer between the first media channel and the first central cavity.

13. The apparatus of claim 12, wherein the tissue is stimulatable via the first electrode and the second electrode.

14. The apparatus of claim 13, further comprising:

a second cavity in the body;

a third plurality of anchor pins positioned within the second cavity;

a fourth plurality of anchor pins within the second cavity;

the second cavity having a second central cavity between the third plurality of anchor pins and the fourth plurality of anchor pins;

the second cavity including a second media channel having a first leg positioned outside of the third plurality of anchor pins and extending substantially continuously to a second leg positioned outside the fourth plurality of anchor pins with respect to the second central cavity, the second media channel in fluid communication with the second central cavity through openings between individual pins of the third plurality of anchor pins and through openings between individual pins of the fourth plurality of anchor pins, wherein the openings between individual pins of the third plurality of anchor pins and the openings between individual pins of the fourth plurality of anchor pins restrict complete fluid transfer between the second media channel and the second central cavity and allow molecular migration between the second media channel and the second central cavity;

a third post positioned in the second central cavity;

a fourth post positioned in the second central cavity;

a third port located in the first end of the body and in communication with the second media channel; and a fourth port located in the first end of the body and in communication with the second media channel.

15. The apparatus of claim 14, further comprising a third electrode and a fourth electrode positioned adjacent to the second cavity.

16. The apparatus of claim 15, further comprising:

a third cavity in the body;

a fifth plurality of anchor pins positioned within the third cavity;

a sixth plurality of anchor pins within the third cavity;

the third cavity having a third central cavity between the fifth plurality of anchor pins and the sixth plurality of anchor pins;

the third cavity including a third media channel having a first leg positioned outside of the fifth plurality of anchor pins and extending substantially continuously to a second leg positioned outside the sixth plurality of anchor pins with respect to the third central cavity, the third media channel in fluid communication with the third central cavity through openings between individual pins of the fifth plurality of anchor pins and through openings between individual pins of the sixth plurality of anchor pins, wherein the openings between individual pins of the fifth plurality of anchor pins and the openings between individual pins of the sixth plurality of anchor pins restrict complete fluid transfer between the third media channel and the third central cavity and allow molecular migration between the third media channel and the third central cavity;

a fifth post positioned in the third central cavity;

a sixth post positioned in the third central cavity;

a fifth port located in the first end of the body and in communication with the third media channel; and a sixth port located in the first end of the body and in communication with the third media channel.

17. The apparatus of claim 16, further comprising a fifth electrode and a sixth electrode positioned adjacent to the third cavity.

18. The apparatus of claim 17, further comprising:

a fourth cavity in the body;

a seventh plurality of anchor pins positioned within the fourth cavity;

an eighth plurality of anchor pins within the fourth cavity;

the fourth cavity having a fourth central cavity between the seventh plurality of anchor pins and the eighth plurality of anchor pins;

the fourth cavity including a fourth media channel having a first leg positioned outside of the seventh plurality of anchor pins and extending substantially continuously to a second leg positioned outside the eighth plurality of anchor pins with respect to the fourth central cavity, the fourth media channel in fluid communication with the fourth central cavity through openings between individual pins of the seventh plurality of anchor pins and through openings between individual pins of the eighth plurality of anchor pins, wherein the openings between individual pins of the seventh plurality of anchor pins and the openings between individual pins of the eighth plurality of anchor pins restrict complete fluid transfer between the fourth media channel and the fourth central cavity and allow molecular migration between the fourth media channel and the fourth central cavity;

a seventh post positioned in the fourth central cavity;

15

16 an eighth post positioned in the fourth central cavity;

a seventh port located in the first end of the body and in communication with the fourth media channel; and an eighth port located in the first end of the body and in communication with the fourth media channel.

19. The apparatus of claim 18, further comprising a seventh electrode and an eighth electrode positioned adjacent to the fourth cavity.

* * * * *